(12) United States Patent
Ahn

(10) Patent No.: US 10,258,370 B2
(45) Date of Patent: Apr. 16, 2019

(54) VAGINAL ENDOSCOPIC PORT UNIT MODULE

(71) Applicant: KOREA UNIVERSITY RESEARCH AND BUSINESS FOUNDATION, Seoul (KR)

(72) Inventor: Ki Hoon Ahn, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 98 days.

(21) Appl. No.: 15/594,120

(22) Filed: May 12, 2017

(65) Prior Publication Data

US 2017/0252063 A1 Sep. 7, 2017

Related U.S. Application Data

(63) Continuation of application No. 14/411,366, filed as application No. PCT/KR2013/005784 on Jun. 28, 2013, now Pat. No. 9,681,890.

(30) Foreign Application Priority Data

Jun. 28, 2012 (KR) ........................ 10-2012-0069954

(51) Int. Cl.
*A61B 1/00* (2006.01)
*A61B 17/34* (2006.01)
(Continued)

(52) U.S. Cl.
CPC ...... *A61B 17/3423* (2013.01); *A61B 1/00154* (2013.01); *A61B 1/303* (2013.01);
(Continued)

(58) Field of Classification Search
CPC ............ A61B 17/3423; A61B 17/3132; A61B 17/0218; A61B 17/42; A61B 17/345;
(Continued)

(56) References Cited

U.S. PATENT DOCUMENTS 8,187,178 B2 5/2012 Bonadio et al.
2003/0085373 A1 5/2003 Dehdashtian
(Continued)

FOREIGN PATENT DOCUMENTS

CN 103405251 A 11/2013
EP 1345648 9/2003
(Continued)

OTHER PUBLICATIONS

European Search Report completed on Dec. 23, 2015.

*Primary Examiner* — Timothy J Neal
(74) *Attorney, Agent, or Firm* — Rabin & Berdo, P.C.

(57) ABSTRACT

The present invention relates to a laparoscopic port unit module in which one end thereof and the other end are placed inside and outside the human body, respectively, through the vaginal inlet, and provides a vaginal endoscopic port unit module comprising: an outer unit of which the end is exposed to the outside of the vaginal inlet and which comprises one or more outer ports allowing the entry of a surgical instrument including an endoscope; an inner unit formed at the inner wall of the vaginal canal so as to be placed at an incision region connected to the abdominal cavity and allowing the surgical instrument entering through the outer port to come in and out of the abdominal cavity; and a runner unit for connecting the outer unit and the inner unit.

10 Claims, 10 Drawing Sheets

(51) Int. Cl.
    *A61B 1/303*     (2006.01)
    *A61B 1/313*     (2006.01)
    *A61B 17/42*     (2006.01)
    *A61B 17/02*     (2006.01)
    *A61B 17/00*     (2006.01)
    *A61M 39/06*     (2006.01)
    *A61B 90/40*     (2016.01)

(52) U.S. Cl.
    CPC .......... *A61B 1/3132* (2013.01); *A61B 17/0218* (2013.01); *A61B 17/42* (2013.01); *A61B 17/3431* (2013.01); *A61B 17/3462* (2013.01); *A61B 17/3498* (2013.01); *A61B 90/40* (2016.02); *A61B 2017/00278* (2013.01); *A61B 2017/00473* (2013.01); *A61B 2017/00477* (2013.01); *A61B 2017/00862* (2013.01); *A61B 2017/00867* (2013.01); *A61B 2017/345* (2013.01); *A61B 2017/347* (2013.01); *A61B 2017/3425* (2013.01); *A61B 2017/3441* (2013.01); *A61B 2017/3443* (2013.01); *A61B 2017/3449* (2013.01); *A61B 2017/3466* (2013.01); *A61B 2017/3488* (2013.01); *A61B 2017/4216* (2013.01); *A61B 2017/4233* (2013.01); *A61B 2217/007* (2013.01); *A61M 2039/0646* (2013.01)

(58) Field of Classification Search
    CPC .......... A61B 17/3449; A61B 17/00862; A61B 1/00154; A61B 1/303; A61B 1/3132
    See application file for complete search history.

(56) References Cited

U.S. PATENT DOCUMENTS

| | | | |
|---|---|---|---|
| 2005/0251192 A1* | 11/2005 | Shluzas | ............... A61B 17/02 606/191 |
| 2008/0287740 A1 | 11/2008 | Weitzner et al. | |
| 2009/0036745 A1 | 2/2009 | Bonadio et al. | |
| 2009/0112062 A1 | 4/2009 | Bakos | |
| 2010/0204548 A1 | 8/2010 | Bonadio et al. | |
| 2010/0217087 A1 | 8/2010 | Bonadio et al. | |
| 2010/0249694 A1 | 9/2010 | Choi et al. | |
| 2010/0292541 A1 | 11/2010 | Hashiba et al. | |
| 2011/0009704 A1 | 1/2011 | Marczyk et al. | |
| 2011/0071359 A1 | 3/2011 | Bonadio et al. | |
| 2011/0105850 A1 | 5/2011 | Voegele et al. | |
| 2012/0083661 A1 | 4/2012 | Rockrohr | |
| 2013/0060093 A1 | 3/2013 | Bonadio et al. | |

FOREIGN PATENT DOCUMENTS

| | | |
|---|---|---|
| KR | 10-0936926 B1 | 1/2010 |
| KR | 10-2011-0111648 A | 10/2011 |
| KR | 10-2011-0138696 A | 12/2011 |
| WO | WO 2010-009070 A1 | 1/2010 |
| WO | WO 2011-162491 A2 | 12/2011 |

\* cited by examiner

VAGINAL ENDOSCOPIC PORT UNIT MODULE

CROSS-REFERENCE TO RELATED APPLICATION

This is a continuation of co-pending U.S. application Ser. No. 14/411,366, filed Dec. 24, 2014 and allowed on Feb. 16, 2017. This application claims the priority benefit of Korean Patent Application No. 10-2012-0069954, filed on Jun. 28, 2012, in the Korean Intellectual Property Office, the disclosure of which is incorporated herein by reference.

TECHNICAL FIELD

The present invention relates to a vaginal endoscopic port unit module, and more particularly, to a medical instrument including a port that induces the entry of a surgical instrument such as an endoscope for performing a minimally invasive surgery.

BACKGROUND ART

Along with the development of medical technology and equipment, a variety of surgical methods have been proposed. In particular, many advancements are being made in the research and equipment of a minimally invasive surgery technique using an endoscope in the field of a laparoscopic or pelviscopic surgery.

When a lesion occurs in any organ inside an abdominal cavity, the frequency of a laparotomy performed for the treatment of the lesion is remarkably reduced by virtue of the advancement of the minimally invasive surgery technique. A typical laparoscopic surgery requires that one or more openings should be created into the abdomen. This laparoscopic surgery is advantageous in that the magnitude and intensity of pain felt by a patient is reduced and any vestige of a wound is also reduced as compared to the laparotomy.

However, the conventional laparoscopic surgery entails a problem in that an artificial scar remains on the surface of the skin of the patient along with any pain. As a part of the minimally invasive surgery technique to minimize the vestige and the pain, a single-port laparoscopic surgery is actively performed in which the surgeon operates through the patient's umbilicus as a single access point. Nevertheless, the single-port laparoscopic surgery still involves a problem in that pain and scar may remain due to an increase in the size of a wound. Thus, it can be contemplated that the most minimally invasive surgery technique is a surgery performed using a body region or organ such as vagina, anus, urethra, mouth, or nose, which is innately formed when human infant are born.

However, in case of the innaltely formed body region or organ such as vagina, anus, urethra, mouth, or nose, in order for a patient to undergo an operation for an organ inside the abdominal cavity, his or her intestine or urinary bladder must be perforated, which involves a risk that the contents of the intestine or urine will be exposed to the inside of the abdominal cavity.

DISCLOSURE OF INVENTION

Technical Problem

Accordingly, the present invention has been made to solve the above-mentioned problems occurring in the prior art, and it is an object of the present invention to provide a vaginal endoscopic port unit module for laparoscopic surgery, which can gain access into the abdominal cavity via a patient's vagina to minimize her pain and scar in performing a minimally invasive surgery on an organ lesion inside the abdominal cavity.

Technical Solution

To achieve the above object, in one aspect, the present invention provides a vaginal endoscopic port unit module for laparoscopic surgery, which is positioned at one end thereof inside the human body and at the other end thereof outside the human body through a vaginal orifice, the module including: an outer unit whose end is disposed so as to be exposed to the outside of the vaginal orifice and which includes one or more outer ports configured to permit entry of a surgical instrument including an endoscope; an inner unit disposed at an incision site formed on the inner wall of the vaginal canal so as to fluidically communicate with the abdominal cavity, and configured to include an inner port permitting introduction and withdrawal of the surgical instrument introduced thereto through the outer port into and from the abdominal cavity; and a runner unit configured to connect the outer unit and the inner unit with each other.

In the vaginal endoscopic port unit module, the inner unit may be implemented as an elastic structure so as to be inserted into the incision site formed on the inner wall of the vaginal canal.

In the vaginal endoscopic port unit module, the inner unit may include: an inner unit header configured to pass through the incision site 2 formed on the inner wall of the vaginal canal and then to be introduced into the abdominal cavity; an inner unit body connected at one end thereof to the inner unit header 310 and configured such that the outer periphery thereof can be maintained in a contact state with the incision site formed on the inner wall of the vaginal canal; and an inner unit tail connected to the other end of the inner unit body 320 and configured such that it can be disposed at the vaginal canal.

In the vaginal endoscopic port unit module, a maximum effective radius of the inner unit header may be larger than that of the inner unit body when viewed from a plane perpendicular to a longitudinal direction passing through the inner unit body and the inner unit header.

In the vaginal endoscopic port unit module, the inner unit header may further include a header stopper formed at an end thereof, which is oriented toward the inner unit tail, so as to be in close contact with the inner surface of the incision site formed on the inner wall of the vaginal canal if the inner unit header is stretched toward the outer unit.

In the vaginal endoscopic port unit module, one end of the inner unit header, which is opposite to the header stopper, may have a conical structure for allowing the inner unit header to be easily introduced through the incision site formed on the inner wall of the vaginal canal.

In the vaginal endoscopic port unit module, one end of the inner unit header, which is opposite to the header stopper, may have a diffuser structure that is widened after the insertion thereof into the incision site formed on the inner wall of the vaginal canal.

In the vaginal endoscopic port unit module, the module may further include a connector unit interposed between the runner unit and the inner unit so as to connect the runner unit and the inner unit with each other.

In the vaginal endoscopic port unit module, the connector unit may have a threaded ring structure, and may include a runner connector disposed at the runner unit and an inner connector disposed at the inner unit so that the inner connector can be engagedly fastened to the runner connector.

In the vaginal endoscopic port unit module, the module may further include a connector unit of a ring structure disposed at an end of the runner unit in such a manner as to be interposed between the runner unit and the inner unit so as to connect the runner unit and the inner unit with each other, and the inner unit tail of the inner unit can be inserted into the runner unit through the ring structure.

In the vaginal endoscopic port unit module, the outer port may include an outer port flap configured to permit inflow of fluid to the runner unit while preventing outflow of the fluid from the runner unit, the outer port flap having an inclined portion formed at an end thereof so as to be sharply pointed toward the runner unit, the inclined portion having a pair of sloping grooves formed on the outer surface thereof to increase the surface area of the inclined portion.

In another aspect, the present invention provides a vaginal endoscopic port unit module for laparoscopic surgery, which is positioned at one end thereof inside the human body and at the other end thereof outside the human body through a vaginal orifice, the module including: an outer unit whose end is disposed so as to be exposed to the outside of the vaginal orifice and which includes one or more outer ports configured to permit entry of a surgical instrument including an endoscope; an inner unit disposed at an incision site formed on the inner wall of the vaginal canal so as to fluidically communicate with the abdominal cavity, and configured to permit introduction and withdrawal of the surgical instrument introduced thereto through the outer port into and from the abdominal cavity; and a runner unit configured to connect the outer unit and the inner unit with each other, wherein the inner unit includes an excised tissue guide part for guiding an excised tissue inside the abdominal cavity.

Advantageous Effects

The vaginal endoscopic port unit module according to the embodiments of the present invention as constructed above have the following advantageous effects.

First, the vaginal endoscopic port unit module according to an embodiment of the present invention enables a laparoscopic surgery using the minimally invasive surgery technique to be performed on a body organ innately formed inside the abdominal cavity, thereby minimizing a patient's pain through the minimization of the incision site.

Second, the vaginal endoscopic port unit module according to an embodiment of the present invention enables the minimally invasive surgery technique to be applied to an innately formed body organ so that scar is excluded on the patient's skin even after a surgical operation due to absence of a wound on the surface of the incision site during the surgery procedure, thereby providing an excellent aesthetic effect.

Third, the vaginal endoscopic port unit module according to an embodiment of the present invention enables the minimally invasive surgery technique to be applied to an innately formed body organ so that a patient's admission period can be minimized after a laparoscopic surgery.

Fourth, the vaginal endoscopic port unit module according to an embodiment of the present invention enables the minimally invasive surgery technique to be applied to an innately formed body organ so that a patient's admission period and pain can be minimized, and a separate aesthetic treatment is excluded after a laparoscopic surgery, thereby minimizing the treatment cost of the patient.

Fifth, the vaginal endoscopic port unit module according to an embodiment of the present invention enables smooth withdrawal of excised tissue through the excised tissue guide part during a surgical procedure.

BRIEF DESCRIPTION OF THE DRAWINGS

The above and other objects, features and advantages of the present invention will be apparent from the following detailed description of the preferred embodiments of the invention in conjunction with the accompanying drawings, in which.

BEST MODE FOR CARRYING OUT THE INVENTION

Figure 1:
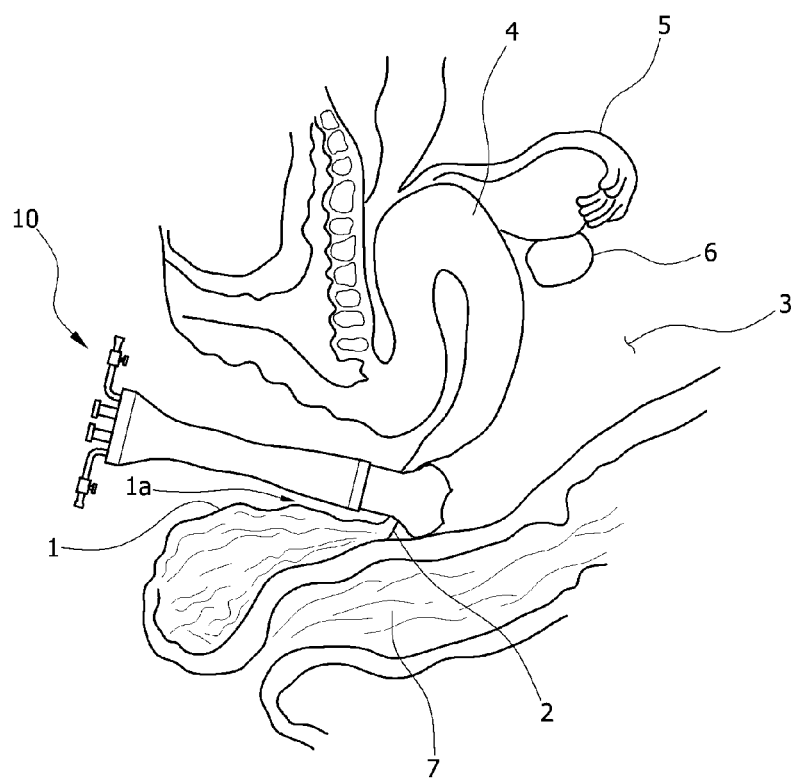
FIG. 1 is a diagrammatic view illustrating a state in which a vaginal endoscopic port unit module according to an embodiment of the present invention is introduced into a human body.

Now, preferred embodiments of a vaginal endoscopic port unit module according to the present invention will be described hereinafter in detail with reference to the accompanying drawings. However, the present invention is not limited to embodiments disclosed below, but may be implemented in various different forms. Embodiments are provided only for illustrative purposes and for full understanding of the scope of the present invention by those skilled in the art.

A vaginal endoscopic port unit module 10 for laparoscopic surgery according to an embodiment of the present invention is introduced into a human body through a vaginal orifice and then is disposed at an incision site formed on the inner wall of the vaginal canal to allow the vaginal canal to fluidically communicate with the abdominal cavity so that a surgical instrument including an endoscope can enter the abdominal cavity via the vaginal canal.

The vaginal endoscopic port unit module 10 according to an embodiment of the present invention includes an outer unit 100, a runner unit 200, and an inner unit 300. The vaginal endoscopic port unit module 10 can be introduced into the vaginal canal 1a via the vaginal orifice 1. An incision site 2 is formed on the inner wall of the vaginal canal 1a so that the inner unit 300 is disposed at the incision site 2. A surgical instrument such as an endoscope can be inserted into the vaginal canal 1a through the outer unit 100 positioned at the outside of the vaginal canal 1a, and can be introduced into the abdominal cavity 3 via the runner unit 200 and the inner unit 300. A surgery can be performed on an organ such as uterus 4, uterine tube/fallopian tube 5, or ovary 6 by means of the surgical instrument introduced into the abdominal cavity 3. Although female gynecological organs have been illustrated and described in this embodiment, the present invention can be applied to various body organs, which enable easy access to the abdominal cavity by achieving the introduction of the surgical instrument into the abdominal cavity via the inner wall of the vaginal canal. In view of this fact, the laparoscope minimally invasive surgery can be performed on various body organs including intraperitoneal and retroperitoneal organs such as gastrointestinal tract including appendix, gallbladder, and kidneys, besides the female gynecological organs.

The outer unit 100 is disposed at an end thereof at the outside of a vaginal orifice and includes one or more outer ports 120 that allow for entry of a surgical instrument including an endoscope (not shown). The outer unit 100 includes an outer housing 110 and one or more outer ports 120.

The outer housing 110 is connected to an end of the runner unit 200 so that the internal space of the runner unit 200 which will be described later can be separated from the external space of the runner unit 200. One or more outer ports 120 are formed on one surface of the outer housing 110.

The outer ports 120 allow for entry of surgical instruments such as an endoscope (not shown) and the like so that the surgical instruments can be introduced into the abdominal cavity via the runner unit 200 and the inner unit 300. Each of the outer ports 120 has a through-hole 121 formed at the center thereof so that a surgical instrument such as an endoscope (not shown) can be inserted and mounted in the module through the through-hole 121.

The outer port 120 is protrudingly formed on one surface of the outer housing 110 and includes an outer port line 122 formed extendingly from the outer housing 110 in a tightly sealed state. An outer port flap 130 is disposed in the outer port line 122. The outer port flap 130 (see FIG. 7) permits the introduction of a surgical instrument such as an endoscope (not shown) introduced into the outer port 120 through the through-hole 121 of the outer port 120 into the runner unit 200 while preventing the outflow of blood, infusion solution, body fluid, some tissues, and the like from the abdominal cavity, and the outflow of gas injected for delivery of light to the inside of the abdominal cavity, or acquisition of image information or performance of surgery in the abdominal cavity through the outer port 120.

Figure 7:
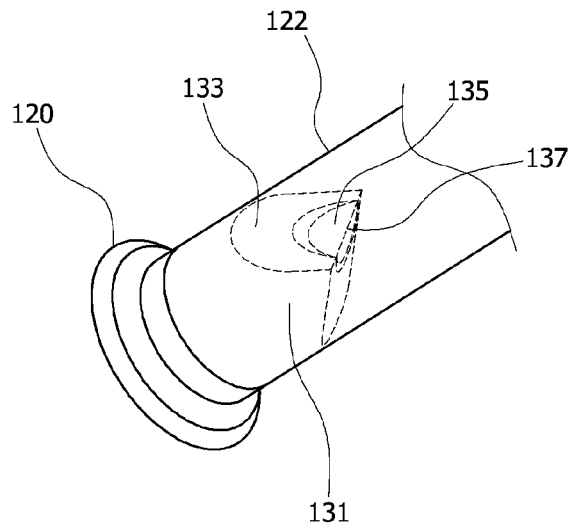
FIGS. 7 to 9 are a schematic state view and a partial cross-sectional view illustrating before and after the operation of an outer port flap inside an outer port of an outer unit of a vaginal endoscopic port unit module according to an embodiment of the present invention.
Figure 8:
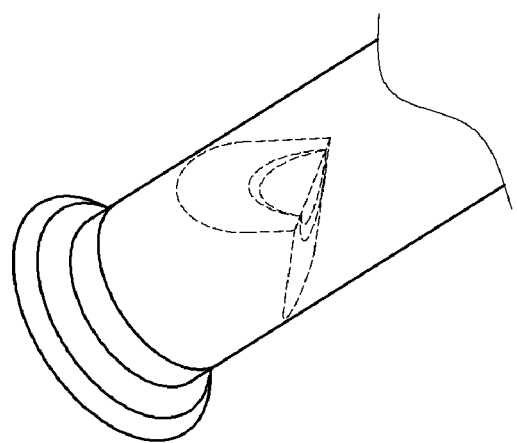

The outer port flap 130 which is disposed in the outer port line 122 includes a flap body 131 and an opening portion 137. The flap body 131 has a structure in which an inner portion of the flap body 131 is connected to an end thereof where the through-hole 121 is formed inside the outer port line 122 of the outer port 120. The opening portion 137 has a structure in which it is maintained in a closed state at normal times but is widened to a given degree of opening by an external force. In other words, as shown in FIGS. 7 and 8, the opening portion 137 is maintained in a closed state at normal times whereas if a certain surgical instrument is introduced into the outer port 120 through the through-hole 121 and a pressure is formed at the through-hole 121 side of the flap body 131, the flap body 131 is deformed to take a structure in which the opening portion 137 is naturally opened.

As such, the flap body 131 is disposed inside the outer port 120 so as to function to prevent leakage of body fluid or gas as mentioned above by dividing a space.

Figure 9:
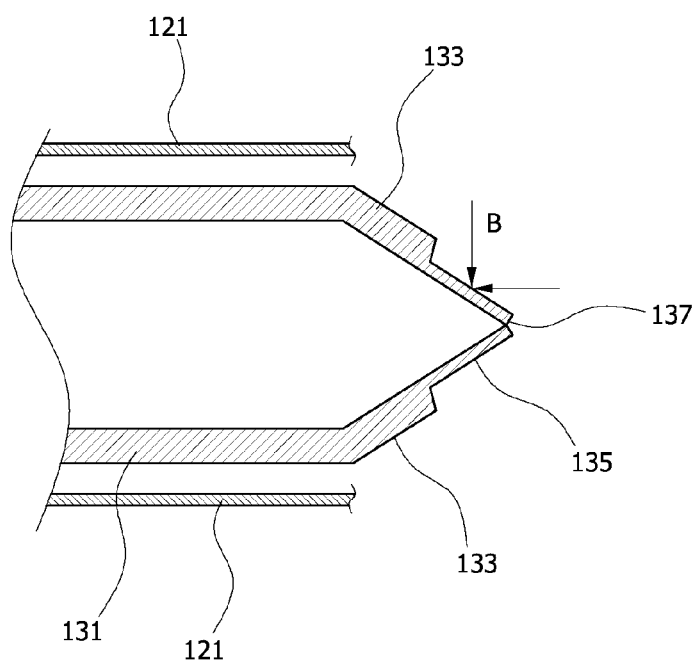

The outer port flap 130 has an inclined portion 133 formed at an end thereof, which is opposite to the through-hole 121, so as to be sharply pointed toward the runner unit 200. By virtue of this configuration of the inclined portion 133, the opening portion 137 of the outer port flap 130 is prevented from being widened by being pressed by a pressure of body fluid or gas from the runner unit 200 and is maintained in a closed state. In addition, the inclined portion 133 has a pair of sloping grooves 135 formed on the outer surface thereof so as to be oriented toward the runner unit 200. As shown in FIGS. 7 to 9, the sloping grooves 135 are formed on the outer surface of the inclined portion 133 so as to take a structure of increasing the pressurized area of the sloping grooves 135, which is indicated by an arrow B, by the pressure of body fluid or gas from the runner unit 200, thereby promoting the maintenance of a state in which the opening portion 137 is automatically closed. Further, a region where the sloping groove 135 is formed may have a thickness smaller than that of the inclined portion 133 except the sloping groove, if necessary, so that the region where the sloping groove 135 is formed has a greater possibility of being deformed than the remaining region of the inclined portion 133 other than the sloping groove even after the introduction of the surgical instrument into the outer port 120. Thus, the degree of opening of the opening portion 137 can be minimized by body fluid or gas from the runner unit 200, thereby preventing or minimizing leakage of the body fluid or gas through the outer port 120.

The outer unit 100 can includes an outer inflow/outflow line part 140; 140a, 140b. The outer inflow/outflow line part 140; 140a, 140b preferably has a structure in which at least two outer inflow/outflow line parts are arranged so as to be opposed to each other. In other words, the outer inflow/outflow line part 140 includes a line body 142, a line port 143, and a line valve 141. The line body 142 is connected at one end thereof to the outer housing 110 and has the line port 143 formed at the other end thereof. The line valve 141 is disposed on a line of the line body 142 so that the fluidic communication between the internal space of the outer unit 100 and the outside through the line port 143 can be controlled. The line port 143 of the outer inflow/outflow line part 140 is connected to a gas supply unit (not shown) so that gas can be supplied into the abdominal cavity through the outer unit 100, the runner unit 200, and the inner unit 300, or body fluid flowed out of the body region such as the abdominal cavity and then flowed into the runner unit 200 can be discharged to the outside. In the case where the outer inflow/outflow line part 140 is provided in plural numbers, if necessary, smooth inflow and outflow of gas and liquid can be achieved simultaneously through an opposed arrangement of the plural outer inflow/outflow line parts 140. In addition, the outer inflow/outflow line part can be provided in plural numbers, if necessary, in which case, the plural inflow/outflow line parts 140a, 140b, 140c, and 140d form an equiangularly divided arrangement structure so that outflow of body fluid and inflow of gas can be selectively performed in an easier manner in response to a change in the engagement state of a connector unit.

The runner unit 200 is connected at one end thereof to the outer housing 110 of the outer unit 100, and is made of a flexible material so that smooth introduction of the runner unit 200 into the vaginal canal 1a can be ensured and damage of the inner wall of the vaginal canal can be prevented. The runner unit 200 is connected at the other end thereof to the inner unit 200 side. Although having not definitely been described in this embodiment, the runner unit may have a structure in which it is fixedly mounted to the outer unit so that the runner unit and the outer unit are formed integrally with each other. The runner unit may be constructed in various manners, such as taking a structure in which the runner unit is connected to the outer unit by means of a separate connector unit, if necessary.

The inner unit 300 has a structure in which it can be inserted into the incision site 2 formed on the inner wall of the vaginal canal 1a. In the case where the inner unit 300 is disposed at the incision site 2, one end thereof is positioned at the abdominal cavity side and the other end thereof is positioned inside the vaginal canal 1. The inner unit 300 includes an inner port 305. The inner port 305 permits introduction and withdrawal of a surgical instrument such as an endoscope introduced thereto through the outer unit 100 into and from the abdominal cavity 3.

The inner unit 300 is preferably made of a certain elastic material so as to prevent the inner unit 300 from undesirably escaping from the incision site 2 formed on the inner wall of the vaginal canal while accomplishing the insertion of the inner unit 300 into the incision site 2. In other words, in the case where the inner unit 300 is disposed at the incision site 2, a structure can be easily implemented in which a front end of the inner unit 300 is inserted into the incision site 2 in an elastically deformed state and is introduced into the abdominal cavity 3, and the other end of the inner unit 300 is disposed at the vaginal canal 1a.

Figure 3:
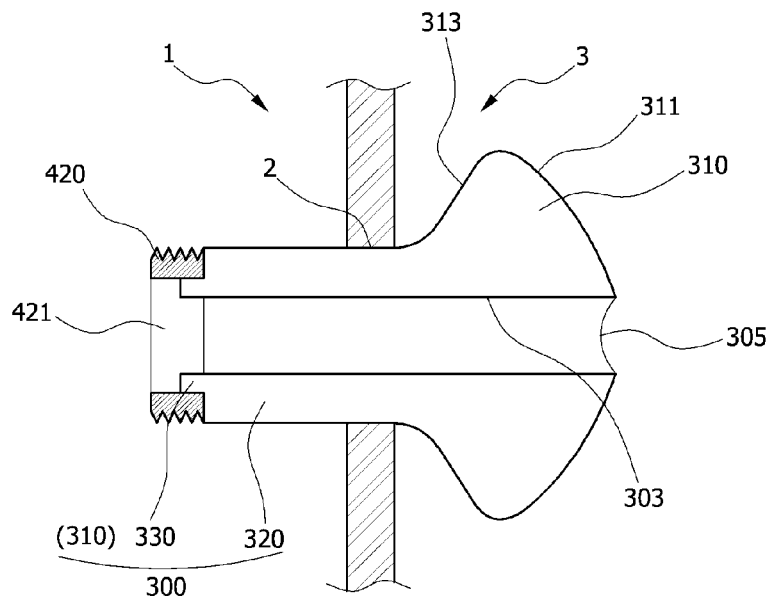
FIG. 3 is a schematic partial cross-sectional view illustrating an inner unit of a vaginal endoscopic port unit module according to an embodiment of the present invention is introduced into a human body.

As shown in FIG. 3, the inner unit 300 according to an embodiment of the present invention includes an inner unit header 310, an inner unit body 320, and an inner unit tail 330. The inner port 305 of the inner unit 300 is formed in the inner unit 300 in such a manner as to penetrate through the inner unit header 310, the inner unit body 320, and the inner unit tail 330. The inner unit header 310 passes through the incision site 2 formed on the inner wall of the vaginal canal and then is introduced into the abdominal cavity 3. The inner unit body 320 is connected at one end thereof to the inner unit header 310, and is configured such that the outer periphery thereof can be maintained in a contact state with the incision site 2 formed on the inner wall of the vaginal canal. The inner unit tail 330 is connected to the other end of the inner unit body 320, and has a structure in which it can be disposed at the vaginal canal. The inner unit tail 330 may have a structure in which it has an outer diameter smaller than that of the inner unit body 320 so as to be connected with an inner connector 420 of a connector unit 400, which will be described later.

Meanwhile, the inner unit 300 according to an embodiment of the present invention may further include a configuration for preventing the inner unit 300 undesirably inserted into the incision site 2 during the surgery procedure from escaping from the incision site 2. In other words, the inner unit 300 has a structure in which a maximum effective radius of the inner unit header 310 is larger than that of the inner unit body 320 when viewed from a plane perpendicular to a longitudinal direction passing through the inner unit body 320 and the inner unit header 310. As shown in FIG. 3, when it is assumed that the length of the incision site is a1, the maximum effective radius of the inner unit header 310 is a2, and the maximum effective radius of the inner unit body 320 is a3, the following relationship is satisfied: a2>a3□a1 so that the inner header 310 is inserted through the incision site 2 in a folded state or to a minimized size, and then returns to an original shape by an elastic restoring force thereof to have a predetermined size, thereby preventing the inner header 310 from undesirably escaping from the incision site 2 after the insertion thereof into the incision site 2.

Moreover, in this case, the inner unit 300 may further include a structure formed in a predetermined shape. In other words, as shown in FIG. 3, the inner unit header 310 may further include a header stopper 313 formed at an end thereof, which is oriented toward the inner unit tail 330, so as to be in close contact with the inner surface of the incision site 2 formed on the inner wall of the vaginal canal when the inner unit header 310 is stretched toward the outer unit 100. The header stopper 313 may be in close contact with the inner surface of the incision sit 2 at the abdominal cavity side so as to prevent the inner unit from undesirably escaping from the incision site 2. In addition, the inner unit header 310 may have a structure in which it has a conical front end 311 so that the inner unit header 310 is easily introduced through the incision site 2 formed on the inner wall of the vaginal canal.

Figure 4:
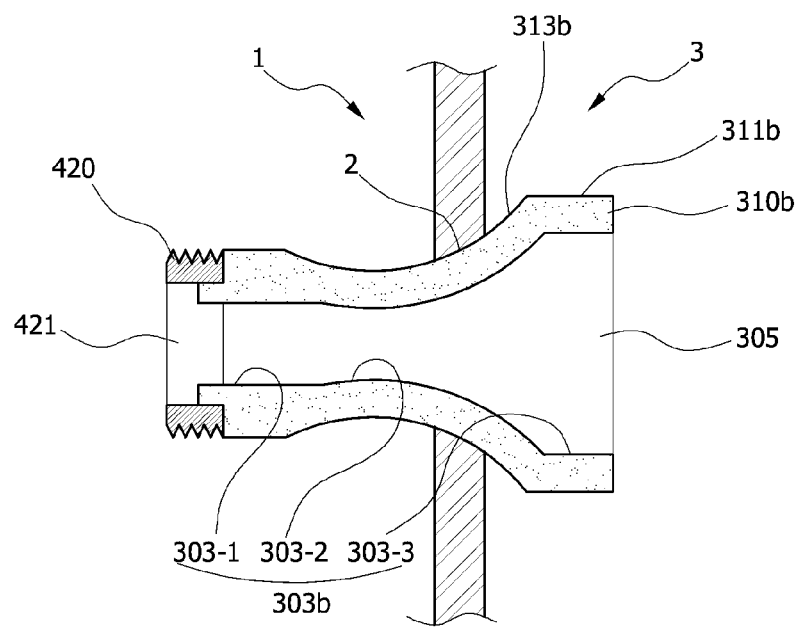
FIG. 4 is a schematic partial cross-sectional view illustrating another example of an inner unit of a vaginal endoscopic port unit module according to an embodiment of the present invention is introduced into a human body.

Also, the inner unit 300 is not limited to the above-mentioned conical structure, but may be modified in various manners depending on the type of surgery. For example, as shown in FIG. 4, an inner unit header 310b may have a diffuser structure. In this case, the inner shape of an inner port 305b may also have a structure of an inner port line 303b; 303-1, 303-2, and 303-3 corresponding to the outer shape of the inner unit 300b, but not a simple rectilinear penetration structure. The inner unit header 310b may have a front end 311b forming a cylindrical shape which is widened after the insertion thereof into the incision site 2, and a header stopper 313b connected with the front end 311b may have a diffuser type curved structure.

Figure 2:
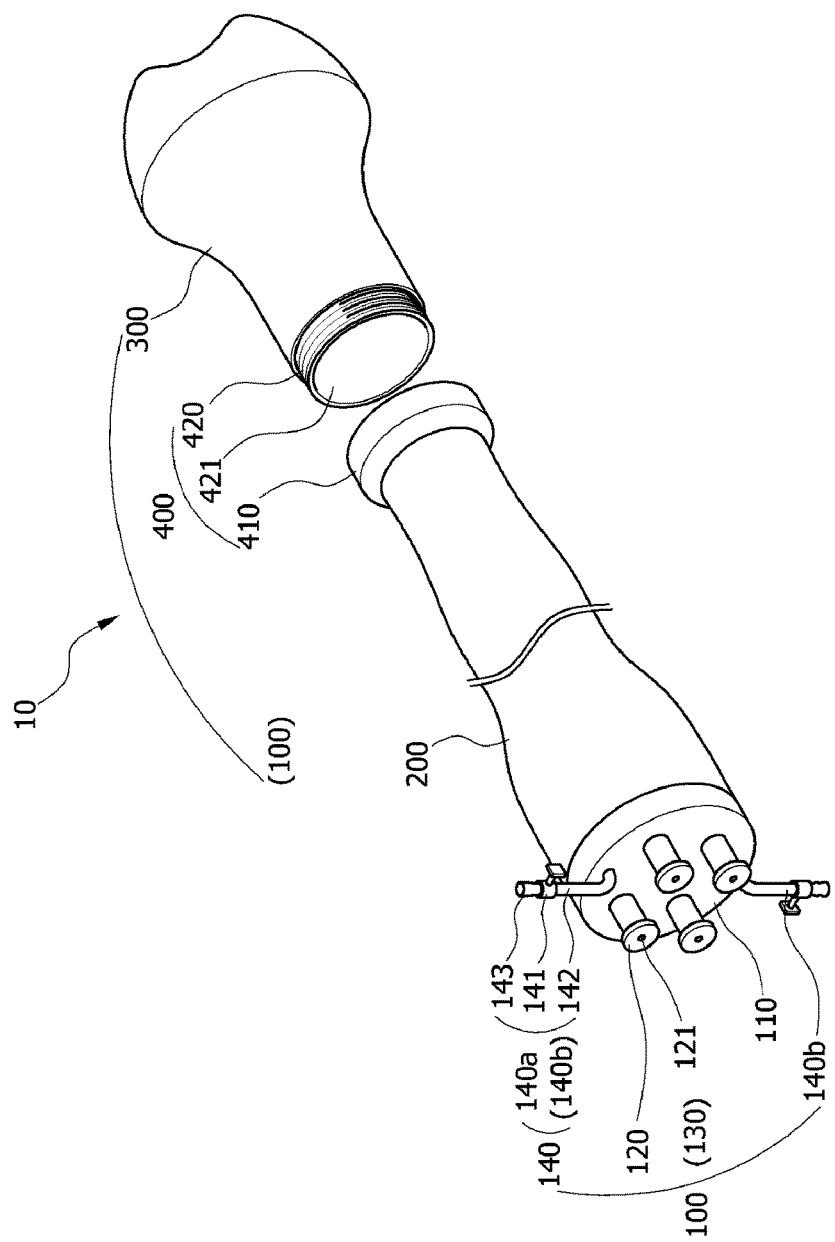
FIG. 2 is a schematic perspective view illustrating a vaginal endoscopic port unit module according to an embodiment of the present invention is introduced into a human body.

In the meantime, the runner unit 200 and the inner unit 300 may be connected to each other by a given fastening structure. In other words, a surgery must be performed in which the inner unit 300 is inserted through the incision site 2 formed on the inner wall of the vaginal canal. In the case where the runner unit and the inner unit are integrally connected with each other, if necessary, smooth mounting of the runner unit and the inner unit may be difficult due to a spatial restriction of the internal space of the vaginal canal. Thus, the runner unit and the inner unit may have a structure in which the inner unit is inserted through the incision site 2 and then is fastened to the runner unit. In this case, the vaginal endoscopic port unit module 10 may further include a connector unit 400 interposed between the runner unit 200 and the inner unit 300. As shown in FIG. 2, the connector unit 400 may have a threaded ring structure. In other words, the connector unit 400 may include a runner connector 410 and an inner connector 420. The runner connector 410 and the inner connector 420 may have a structure in which each of them has a screw thread formed on the inner peripheral surface or outer peripheral surface thereof so that they are engagedly fastened to each other through a common structure such as a common hole 421 formed in the inner connector 420. In the case where air-tightness is preferably formed between the screw threads of the runner connector 410 and the inner connector 420, the formation of the screw thread can be selected in various manners depending on the surgery conditions, such as taking a round screw structure. In addition, the runner connector 410 and the inner connector 420 may be selectively formed of various materials such as a synthetic resin, a metal material and the like depending on design specifications. Although the connector unit having the threaded ring structure has been illustrated in this embodiment, various modifications can be made within a range of implementing a connector having a predetermined insertion type engagement structure.

Figure 5:
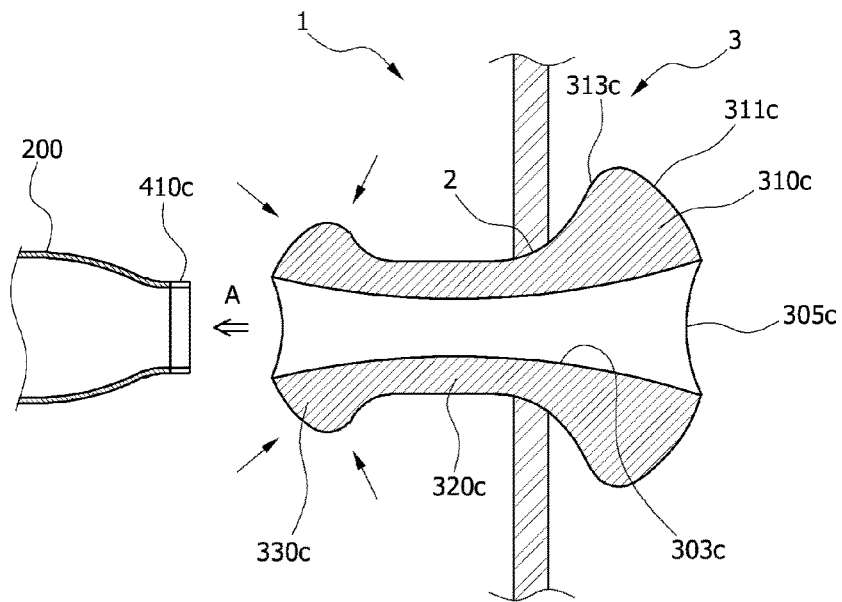
FIGS. 5 and 6 are schematic partial cross-sectional views illustrating another modification of an inner unit and a connector unit of a vaginal endoscopic port unit module according to an embodiment of the present invention is introduced into a human body before and after the connection of the inner unit to a runner unit.
Figure 6:
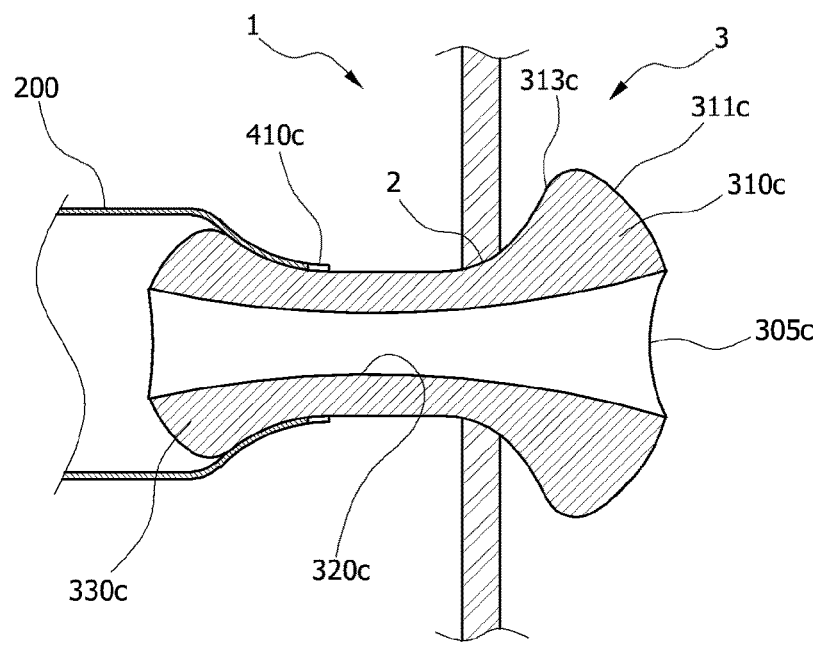
Figure 10:
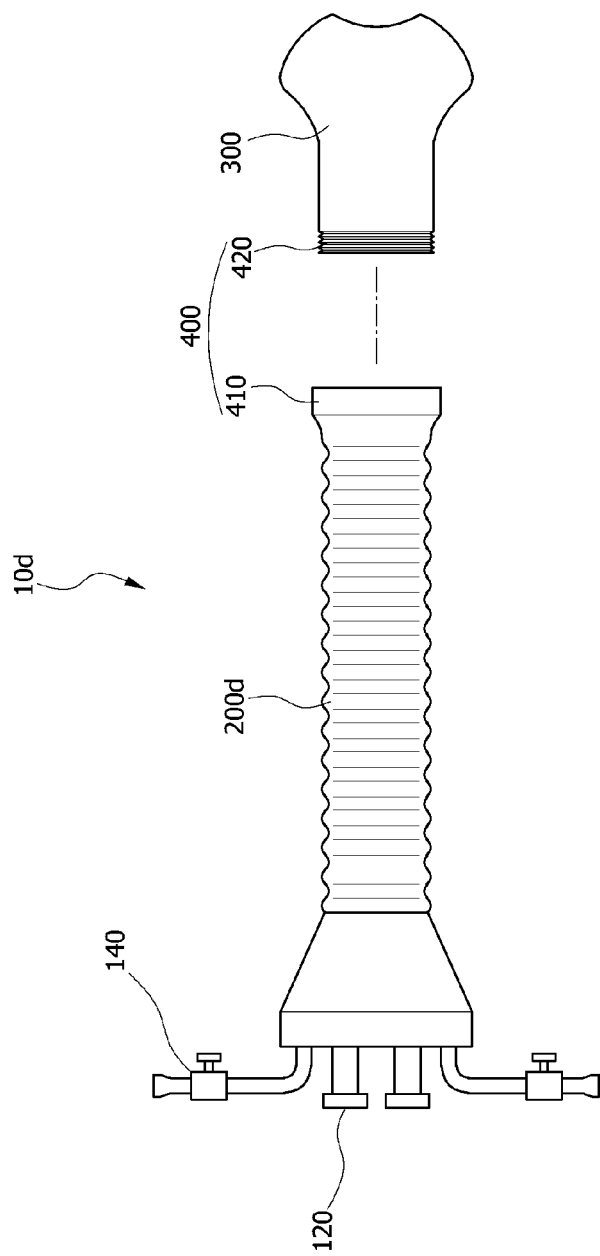
FIG. 10 is a schematic side view illustrating another modification of a runner unit of a vaginal endoscopic port unit module according to an embodiment of the present invention.
Figure 11:
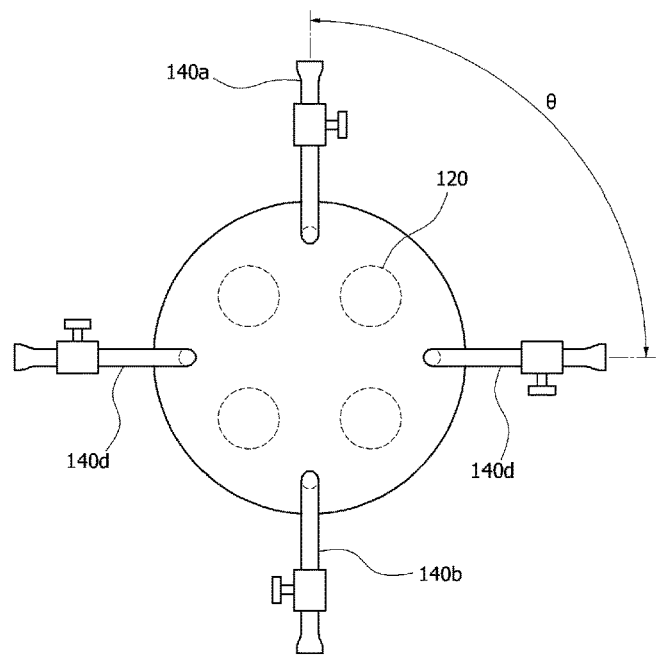
FIG. 11 is a front view illustrating another modification of a outer inflow/outflow line part of an outer unit of a vaginal endoscopic port unit module according to an embodiment of the present invention.

In the meantime, although it has been described in the above-mentioned embodiment that the connector unit is separately mounted on the runner unit and the inner unit, various modifications can be made within a range of implementing a connecting structure of the runner unit and the inner unit. For example, as shown in FIGS. 5 and 6, the connector unit 400c includes a runner connector 410c of a ring structure, and may be implemented as a structure in which the inner unit tail as an end of the inner unit 300 is inserted through the runner connector 410c which in turn performs a given stopping function. In other words, the runner connector 410c of the connector unit 400c of a ring structure can be mounted in the runner unit 200. The runner connector 410c preferably has a diameter smaller than that of the runner unit 200. The inner unit tail 330c preferably has an outer diameter or an effective outer diameter larger than an inner diameter of the runner connector 410c. Although it has been illustrated in this embodiment that the inner unit tail 330c has a conical structure corresponding to that of the inner unit header 310, the present invention is not limited thereto. The inner unit tail 330c can be inserted through the inner periphery of the runner connector 410c after being compressed by a given applied pressure P. Thereafter, the applied pressure P is removed so that the inner unit tail 330c returns to its original shape by an elastic restoring force thereof. Thus, the inner unit tail 330c can be prevented from undesirably escaping from the runner connector 410c having a diameter smaller than that of the inner unit tail 330c. Of course, in this case, the diameter of the inner unit body 320c, the diameter of the inner port 305c, and the inner diameter of the runner connector 410c are preferably formed to establish a predetermined size relationship therebetween in order to prevent the inhibition of the behavior of a surgical instrument such as an endoscope through an inner port 305c In addition, although it has been described in the above-mentioned embodiments that the runner unit 200 is formed of a flexible polymeric material, it may be formed as a structure having a predetermined characteristics. In other words, as shown in FIG. 10, a runner unit 200d of the vaginal endoscopic port unit module 10d may be formed as a bellows type structure. That is, the runner unit 200d of the bellows type structure is connected at one end thereof to the outer unit 100 and is connected at the other end thereof to the inner unit 300 through the connector unit 400. The bellows type runner unit 200d takes a structure in which it is stably arranged inside the vaginal canal 1a through the smooth movement and deformation of the runner unit 200d, but may take a structure which permits the smooth guide and introduction of a surgical instrument such as an endoscope introduced through the outer port 120.

In addition, although it has been described in the above-mentioned embodiments that the constituent elements including the outer unit, the runner unit, the runner unit, and connector unit are constructed independently, various modifications can be made within a range of providing a vaginal endoscopic port unit structure, such as taking a structure in which the elements are wholly or partially formed integrally with each other.

In addition, the inner unit is preferably formed of a deformable material such as silicon or a special rubber material. The outer unit is preferably formed of a soft flexible material. The surface of the vaginal endoscopic port unit module is preferably coated so that the surgical instrument such as the endoscope can be smoothly introduced into or withdrawn from the incision site formed on the inner wall of the vaginal canal, and can be prevented from being damaged.

Meanwhile, in the above embodiments, the inner unit is disposed at the incision site formed on the inner wall of the vaginal canal so as to fluidically communicate with the abdominal cavity, and permits the introduction and withdrawal of the surgical instrument introduced through the outer port into and from the abdominal cavity. The inner unit may further include an excised tissue guide part 360a for guiding an excised tissue inside the abdominal cavity. In FIGS. 12 to 15, there are shown schematic views of a vaginal endoscopic port unit module 10a according to another embodiment of the present invention. In this embodiment, the same configuration as that in the above embodiments is replaced with the above-mentioned configuration and thus a detailed description thereof will be omitted to avoid redundancy.

An inner unit 300a of the vaginal endoscopic port unit module 10a includes an excised tissue guide part 360a. The excised tissue guide part 360a includes deployment frames 320a and 340a, and deployment screens 330a and 350a mounted on the deployment frames 320a and 340a. The excised tissue guide part 360a is surrounded with a guide wrap 302a that can be easily shredded when it is introduced into the incision site formed on the inner wall of the vaginal canal (see FIG. 13). When the inner unit 300a is disposed at the incision site fluidically communicating with the abdominal cavity, the deployment frames 320a and 340a of the excised tissue guide part 360a positioned at a front end of the inner unit 300a contains a shape memory alloy so that they are deployed by the temperature environment in the human body and return to an original shape thereof. The deployment frames 320a and 340a forms a pair, respectively, and are disposed at the upper and lower circumferential end edge of a front end of the inner unit, respectively. When the deployment frames 320a and 340a are deployed, the guide wrap 302a is shredded. The guide wrap 302a may be formed of a material that can be dissolved by its contact with body fluid, if necessary. The deployment frames 320a and 340a includes an upper deployment frame 320a and a lower deployment frame 340a. In this case, two deployment frames 320a are provided at the upper circumferential end edge of the inner unit and two deployment frames 340a are provided at the lower circumferential end edge of the inner unit, but the number of the deployment frames 320a and 340a are not limited thereto. Various modifications of the deployment frames 320a and 340a can be made within a range of stably supporting and protecting some organs which will be described later.

Figure 12:
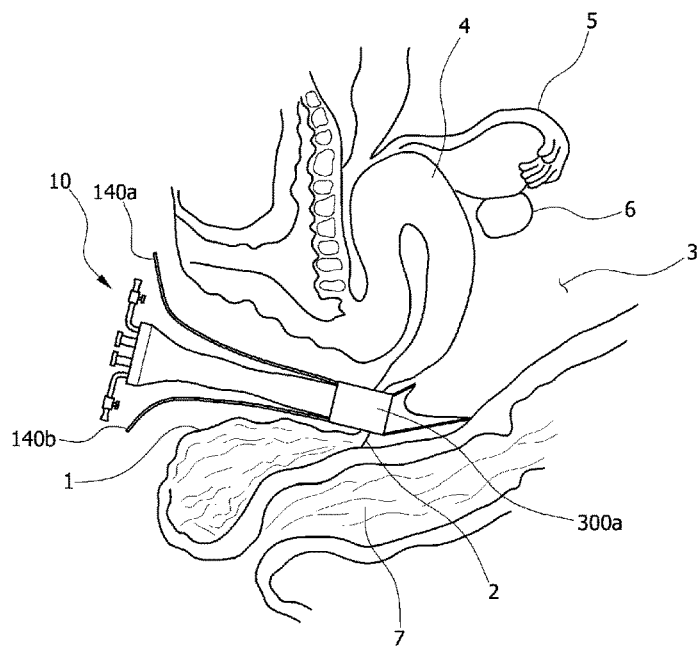
FIGS. 12 to 15 illustrate a schematic state view, and a partial perspective view of a vaginal endoscopic port unit module according to another embodiment of the present invention.
Figure 13:
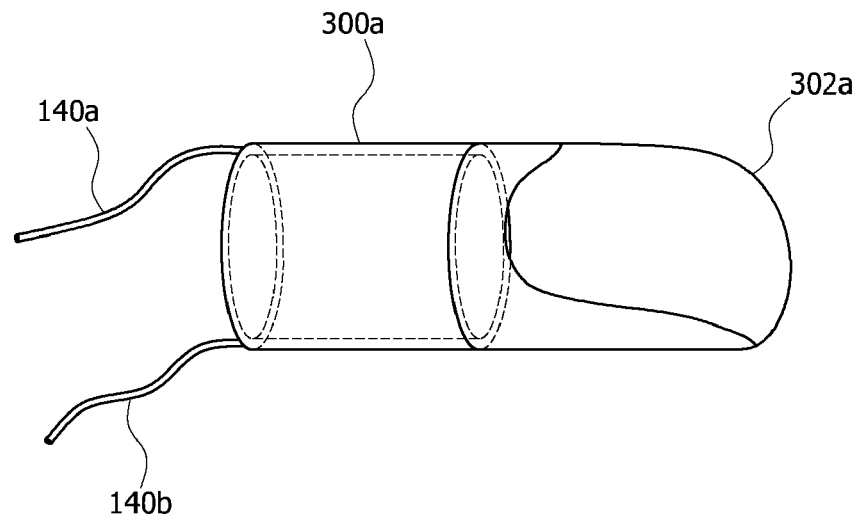
Figure 14:
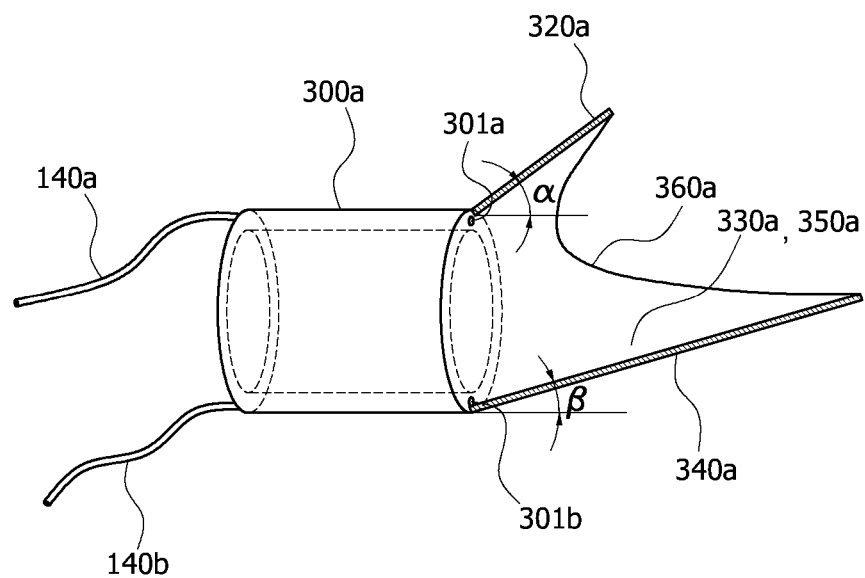
Figure 15:
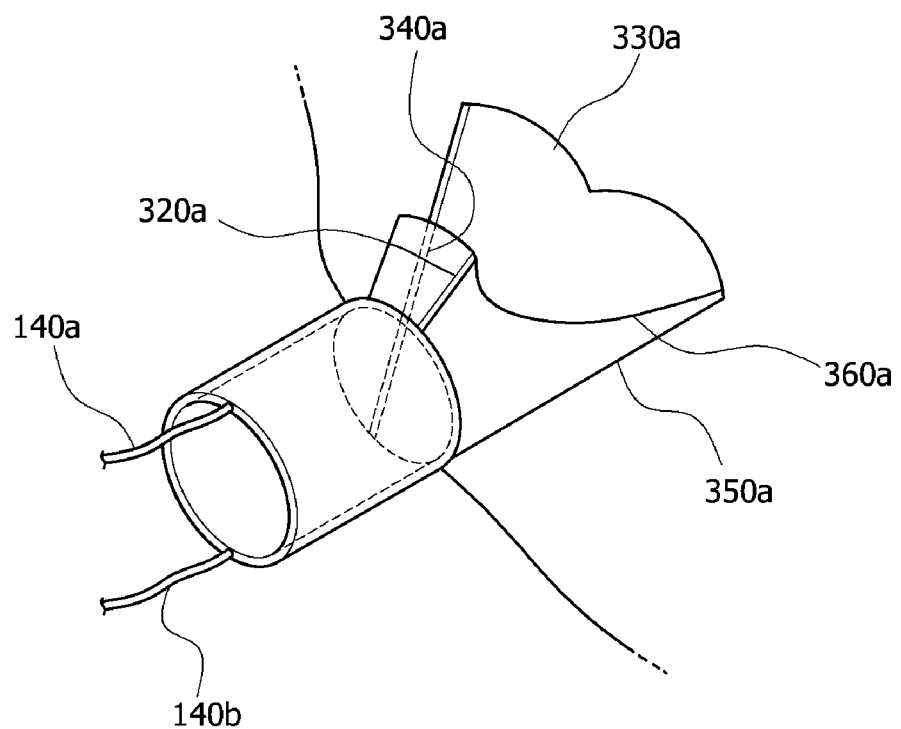

The pairs of the deployment frames 320a and 340a are connected with the deployment screens 350a and 330a so that they perform a supporting or protecting function during the deployment of when the deployment frames 320a and 340a. In FIG. 15, there is shown a state in which the deployment frame is partially hidden by the deployment screen. The deployment frames 320a and 340a can be restricted in rotation by the line of the excised tissue guide part 360a to prevent the upper and lower ends of the deployment frames 320a and 340a from being excessively rotated relative to each other. The deployment frames 320a and 340a form an angle of α and β with respect to a horizontal line segment. The deployment frames 320a and 340a can perform a restriction function against individual tissues with an angular difference occurring during the restoration of the deployment frames 320a and 340a. In other words, as shown in FIG. 12, the upper deployment screen 350a serves to support uterus and the lower deployment screen 330a functions as membranes that protect the small and large intestines inside the abdominal cavity so that when ovary tumor 6 connected to excised suspensory ligament 6a of ovary is excised, the excised tissue is not withdrawn to the outside but can be induced so to be externally withdrawn stably.

In addition, a gas inflow line 140a and a foreign substance outflow line 140b are respectively connected to line throughholes 301a and 301b formed a front end of the inner unit 300a so that a surgeon's visual field can be secured during the surgery procedure through inflow of gas to the abdominal cavity and foreign substances can be smoothly discharged to the outside.

The embodiments as described above are merely illustrative and the invention is not limited to these embodiments. It will be appreciated by a person having an ordinary skill in the art that various equivalent modifications and variations of the embodiments can be made without departing from the spirit and scope of the present invention. Therefore, the true technical scope of the present invention should be defined by the technical spirit of the appended claims.

INDUSTRIAL APPLICABILITY

The vaginal endoscopic port unit module according to the present invention can be variously utilized as a medical instrument within a range of enabling to gain access into the abdominal cavity via a patient's vagina to minimize her pain and scar in performing a minimally invasive surgery on an organ lesion inside the abdominal cavity.

The invention claimed is:

1. A vaginal endoscopic port unit module for laparoscopic surgery, which is positioned at a first end thereof inside the human body and at a second end thereof outside the human body through a vaginal orifice, the module comprising:
an outer unit comprising a proximal end, the proximal end being disposed so as to be exposed to the outside of the vaginal orifice and which includes at least one outer port configured to permit entry of a surgical instrument;
an inner unit configured to be disposed at an incision site formed on the inner wall of the vaginal canal so as to fluidically communicate with the abdominal cavity, and configured to include an inner port permitting introduction and withdrawal of the surgical instrument introduced thereto through the outer port into and from the abdominal cavity; and
a runner unit configured to connect the outer unit and the inner unit with each other, and
wherein the inner unit includes an excised tissue guide part configured to guide an excised tissue inside the abdominal cavity to the inner unit,
wherein the excised tissue guide part includes deployment frames positioned at a front end of the inner unit and deployment screens mounted on the deployment frames, the deployment screens being membranes configured to induce and guide the excised tissue to the inner unit, and
wherein the deployment frames include two upper deployment frames and two lower deployment frames, and the upper deployment frames are provided at the upper circumferential end edge of the inner unit and the lower deployment frames are provided at the lower circumferential end edge of the inner unit.

2. The vaginal endoscopic port unit module according to claim 1, wherein an inner shape of the inner port has a diffuser structure at a portion of the inner unit that is introduced into the abdominal cavity.

3. The vaginal endoscopic port unit module according to claim 1, wherein the excised tissue guide part is surrounded with a guide wrap.

4. The vaginal endoscopic port unit module according to claim 1, wherein the excised tissue guide part is surrounded with a guide wrap, and the guide wrap is formed of a dissolvable material capable of being dissolved by contact with body fluid.

5. The vaginal endoscopic port unit module according to claim 1, wherein the inner unit is implemented as an elastic structure so as to be inserted into the incision site formed on the inner wall of the vaginal canal.

6. The vaginal endoscopic port unit module according to claim 5, wherein the inner unit comprises: an inner unit header configured to pass through the incision site formed on the inner wall of the vaginal canal and then to be introduced into the abdominal cavity; an inner unit body connected at a first end thereof to the inner unit header and configured such that the outer periphery thereof can be maintained in a contact state with the incision site formed on the inner wall of the vaginal canal; and an inner unit tail connected to a second end of the inner unit body and configured such that it can be disposed at the vaginal canal.

7. The vaginal endoscopic port unit module according to claim 6, wherein a maximum effective radius of the inner unit header is larger than that of the inner unit body when viewed from a plane perpendicular to a longitudinal direction passing through the inner unit body and the inner unit header.

8. The vaginal endoscopic port unit module according to claim 1, wherein the outer port comprises an outer port flap configured to permit inflow of fluid to the runner unit while preventing outflow of the fluid from the runner unit, the outer port flap having two opposing inclined portions formed at either side of the outer port flap so as to be sharply pointed toward the runner unit, the inclined portions having a pair of sloping grooves formed on the outer surface thereof.

9. The vaginal endoscopic port unit module according to claim 1, wherein the deployment frames are restricted in rotation by a line of the excised tissue guide part to prevent upper and lower ends of the deployment frames from being excessively rotated relative to each other.

10. The vaginal endoscopic port unit module according to claim 9, wherein each of the deployment frames forms an angle with respect to a horizontal line segment.

* * * * *